US007956207B2

(12) United States Patent
Meiere et al.

(10) Patent No.: US 7,956,207 B2
(45) Date of Patent: Jun. 7, 2011

(54) HETEROLEPTIC ORGANOMETALLIC COMPOUNDS

(75) Inventors: Scott Houston Meiere, Williamsville, NY (US); John D. Peck, West Seneca, NY (US); Ronald F. Spohn, Getzville, NY (US); David M. Thompson, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 775 days.

(21) Appl. No.: 11/899,784

(22) Filed: Sep. 7, 2007

(65) Prior Publication Data

US 2008/0081922 A1    Apr. 3, 2008

Related U.S. Application Data

(60) Provisional application No. 60/847,610, filed on Sep. 28, 2006.

(51) Int. Cl.
*C07F 7/00* (2006.01)
*C07F 11/00* (2006.01)
*C23C 16/00* (2006.01)

(52) U.S. Cl. ............ 556/51; 427/248.1; 534/15; 556/57

(58) Field of Classification Search .................... 556/51, 556/57; 427/248.1; 534/15
See application file for complete search history.

(56) References Cited

U.S. PATENT DOCUMENTS

| | | | |
|---|---|---|---|
| 5,318,935 A * | 6/1994 | Canich et al. ................. | 502/117 |
| 5,389,401 A | 2/1995 | Gordon | |
| 5,789,027 A | 8/1998 | Watkins et al. | |
| 5,814,574 A * | 9/1998 | McNally ....................... | 502/103 |
| 5,976,991 A | 11/1999 | Laxman et al. | |
| 5,980,983 A | 11/1999 | Gordon | |
| 6,015,917 A | 1/2000 | Bhandari et al. | |
| 6,159,855 A | 12/2000 | Vaartstra | |
| 6,287,965 B1 | 9/2001 | Kang et al. | |
| 6,291,867 B1 | 9/2001 | Wallace et al. | |
| 6,342,277 B1 | 1/2002 | Sherman | |
| 6,399,208 B1 | 6/2002 | Baum et al. | |
| 6,541,278 B2 | 4/2003 | Morita et al. | |
| 6,809,212 B2 | 10/2004 | Meiere et al. | |
| 6,869,638 B2 | 3/2005 | Baum et al. | |
| 6,919,468 B2 | 7/2005 | Thompson et al. | |
| 6,960,675 B2 | 11/2005 | Chen et al. | |
| 2004/0043149 A1 | 3/2004 | Gordon et al. | |
| 2005/0023625 A1 | 2/2005 | Ahn et al. | |
| 2005/0075510 A1 | 4/2005 | Meiere et al. | |
| 2005/0215805 A1 | 9/2005 | Meiere | |
| 2006/0046521 A1* | 3/2006 | Vaartstra et al. ............... | 438/778 |
| 2007/0036894 A1* | 2/2007 | Thompson et al. ......... | 427/248.1 |

OTHER PUBLICATIONS

Jourdain et al., Canadian Journal of Chemistry, vol. 78, No. 12, pp. 1570-1574 (2000).*
Lehn et al., Journal of Materials Chemistry, vol. 14, pp. 3239-3245 (2004).*
Burger, H. et al., "Tris(Dialkylamino)Titan-Derivate Der Elemente P Und As (1)", Inorg. Nucl. Chem. Letters, vol. 6, pp. 299-304, Pergamon Press, Great Britain (1970).
Cai, Hu et al., "Amide-Silyl Ligand Exchanges and Equilibria Among Group 4 Amide and Silyl Complexes", Inorg. Chem., vol. 46, No. 19, pp. 8071-8078 (2007).
Chen, Tianniu, et al., "Synthesis, Characterization and X-Ray Structures of New Molybdenum Bis(Imide) Amide and Silyl Complexes", Inorganica Chimica Acta 345, pp. 113-120 (2003).
Weiller, Bruce H., "Chemical Vapor Deposition of Tin From Tetrakis(Dimethylamido)Titanium and Ammonia: Kinetics and Mechanistic Studies of the Gas-Phase Chemistry", J. Am. Chem. Soc. 118, pp. 4975-4983 (1996).
Yu, Xianghua et al., "Unusual Equilibria Involving Group 4 Amides, Silyl Complexes, and Silyl Anions Via Ligand Exchange Reactions", J. Am. Chem. Soc. 126, pp. 4472-4473 (2004).
Anderson, Richard A. Dialkylbis[bis(trimethylsilyl)amido]zirconium(IV) and -hafnium(IV). Preparation and Reaction with Carbon Dioxide and tertg-Butyl Isocyanide. Inorganic Chemistry. vol. 18, No. 10 (1979), pp. 2928-2932. (5 pgs).
Andrianov, K. A. et al. "Coammonolysis of Silicon Tetrachloride and Trimethylchlorosilane". M.V. Lomonosov Moscow Inst. of Fine Chemical Technology. Bull. Acad. Sci., USSR Div. Ch. Sci., 25 (1976), pp. 2432-2435. (4 pgs.).
Bradley, John S. et al. "Syntheses and Structures of $[Me_3N)_3SiNHLi]_4$, $(C_4H_8O)Al[NHSi(NMe_2)_3]_3$, $((Me_2N)_3SiNH)_3Al$ and $Li(THF)_2+[((Me_2N)_3SiNH)_4Al]$". Dalton Transactions (2003), pp. 1846-1851. (6 pgs.).
Crowell, John E. "Chemical Methods of Thin Film Deposition: Chemical Vapor Deposition, Atomic Layer Deposition, and Related Technologies". Journal of Vacuum Science and Technology A: Vacuum, Surfaces, and Films, vol. 21, Issue 5, (Sep. 2003) pp. S88-S95 (8 pgs.).
Fix, Renaud et al. "Chemical Vapor Deposition of Titanium Zirconium, and Hafnium Nitride Thin Films." Chem. Mater. 3 (1991) pp. 1138-1148. (11 pgs.).

(Continued)

*Primary Examiner* — Porfirio Nazario Gonzalez
(74) *Attorney, Agent, or Firm* — Iurie A. Schwartz

(57) ABSTRACT

This invention relates to organometallic compounds represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; a process for producing the organometallic compounds, and a method for producing a film or coating from organometallic precursor compounds.

33 Claims, No Drawings

OTHER PUBLICATIONS

Gordon, Roy G. and Becker, Jill. "Vapor Deposition of Metal Oxides and Silicates: Possible Gate Insulators for Future Microelectronics". Chem. Mater. 13 (2001). pp. 2463-2464. (2 pgs.).

Hendrix, B.C. et al. "Composition Control of $Hf_{1-x}Si_xO_2$ Films Deposited on Si by Chemical-Vapor Deposition Using Amide Precursors". Applied Physics Letters, vol. 80, No. 13 (Apr. 1, 2002), pp. 2362-2364. (3 pgs).

Hoover, Cynthia A. et al. High-K Dielectric Precursors: Synthesis and Deposition. Semiconductor Manufacturing Magazine. Reprint Jun. 2004. (4 pgs.).

Lucovsky, G. and Rayner, Jr., G. B. "Microscopic Model for Enhanced Dielectric Constants in Low Concentration SiO2-rich Noncrystalline Zr and Hf Silicate Alloys". Applied Physics Letters, vol. 77, No. 18. (Oct. 30, 2000), pp. 2912-2914. (3 pgs.).

Nam, Won-Hee and Rhee, Shi-Woo. "Atomic Layer Deposition of Hafnium Silicate Thin Films Using $HfCl_2[N(SiMe_3)_2]_2$ and $H_2O$". Electrochemical and Solid-State Letters, 7(4) (2004) pp. C55-C56. (2 pgs.).

Owyang, Jon and Bartholomew, Larry. "Implementing a Batch Atomic Layer Deposition Approach for Advanced DRAM Dielectrics". Micro Magazine.com, V23, No. 2 (Mar. 2005), pp. 49-55. Downloaded from http://www.micromagazine.com/grabber.php3?URL=http://www.micromagazine.com/arch... download date Sep. 30, 2005. (8 pgs).

Rovai, Riccardo et al. "Non-Oxide Sol—Gel Chemistry: Preparation from Tris (dialkylamino) silazanes of a Carbon-Free, Porous, Silicon Diimide Gel". Angew Chem. Int. Ed. (1999) 38, No. 13/14, pp. 2036-2038. (3 pgs.).

Seo, Minha et al. "Crystallization and Wet Etching Characteristics of Atomic Layer Deposited $HfO_2$ Filmes Using $Hf([N(CH_3)(C2H_5)]_3[OC(CH_3)_3])$ Precursor and $O_3$ Oxidant." (7 pgs), (2006).

Wolfe, D. et al. "Remote Plasma Enhanced-Metal Organic Chemical Vapor Deposition of Zirconium Oxide/Silicon Oxide Alloy, $(ZrO_2)_x(SiO_2)_{1-x}$ (x≦ 0.5), Thin Films for Advanced High-K Gate Dielectrics". Mat. Res. Soc. Symp. Proc. vol. 567 (1999) Materials Research Society. pp. 343-348. (6 pgs.).

* cited by examiner

HETEROLEPTIC ORGANOMETALLIC COMPOUNDS

RELATED APPLICATIONS

This application claims the benefit of U.S. Provisional Application Ser. No. 60/847,610, filed Sep. 28, 2006, which is incorporated herein by reference.

FIELD OF THE INVENTION

This invention relates to heteroleptic organometallic compounds, a process for producing the heteroleptic organometallic compounds, and a method for producing a film or coating from the heteroleptic organometallic precursor compounds.

BACKGROUND OF THE INVENTION

Chemical vapor deposition methods are employed to form films of material on substrates such as wafers or other surfaces during the manufacture or processing of semiconductors. In chemical vapor deposition, a chemical vapor deposition precursor, also known as a chemical vapor deposition chemical compound, is decomposed thermally, chemically, photochemically or by plasma activation, to form a thin film having a desired composition. For instance, a vapor phase chemical vapor deposition precursor can be contacted with a substrate that is heated to a temperature higher than the decomposition temperature of the precursor, to form a metal or metal oxide film on the substrate. Preferably, chemical vapor deposition precursors are volatile, heat decomposable and capable of producing uniform films under chemical vapor deposition conditions.

The semiconductor industry is currently considering the use of thin films of various metals for a variety of applications. Many organometallic complexes have been evaluated as potential precursors for the formation of these thin films. A need exists in the industry for developing new compounds and for exploring their potential as chemical vapor deposition precursors for film depositions.

For chemical vapor deposition and atomic layer deposition applications, a variety of precursors (amides, alkoxides, and chlorides) exist for a variety of elements (e.g., titanium, hafnium, and tantalum). The chemistry of these materials is dominated mainly by homoleptic systems, or complexes with ligand sets made up of one or more identical ligands, for example, tetrakis(dimethylamino)titanium or tetrakis(ethylmethylamino)hafnium. In contrast, heteroleptic systems for this type of material would consist of two or more different ligands, for example, bis(dimethylamino)bis(ethylmethylamino)-hafnium.

Materials with heteroleptic ligands within the same family can be difficult to prepare and purify. The difficulty in preparing and purifying these heteroleptic systems stems from their rapid reactivity, ligand exchange potential, and similar vapor pressures. For example, combining 2 equivalents of amide 'A1' with $HfCl_4$ will typically not lead to exclusively $Hf(A1)_2(Cl)_2$, but instead will lead to a range of statistically distributed $Hf(A1)_x(Cl)_{4-x}$ species (where x=0-4). Therefore, even if a second amide 'A2' is added well after the first, a mixture of compounds of the formula $Hf(A1)_x(A2)_{4-x}$ (where x=0-4) will result. These compounds, due to their similarity, are difficult to isolate cleanly, even by distillation.

In developing methods for forming thin films by chemical vapor deposition or atomic layer deposition methods, a need continues to exist for precursors that preferably are liquid at room temperature, have adequate vapor pressure, have appropriate thermal stability (i.e., for chemical vapor deposition will decompose on the heated substrate but not during delivery, and for atomic layer deposition will not decompose thermally but will react when exposed to co-reactant), can form uniform films, and will leave behind very little, if any, undesired impurities (e.g., halides, carbon, etc.). Therefore, a need continues to exist for developing new compounds and for exploring their potential as chemical vapor and atomic layer deposition precursors for film depositions. It would therefore be desirable in the art to provide precursors that possess some, or preferably all, of the above characteristics.

SUMMARY OF THE INVENTION

This invention relates in part to organometallic compounds represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M.

This invention also relates in part to organometallic compounds represented by the formula $(R_4R_3N)_xM(NR_1R_2)_y$, wherein M is a metal or metalloid; $NR_1R_2$ and $NR_3R_4$ are different; $R_1$ and $R_2$ are the same or different and are a hydrocarbon group or a heteroatom-containing group; $R_1$ and $R_2$ can be combined to form a substituted or unsubstituted, saturated or unsaturated cyclic group; $R_1$ or $R_2$ of one $NR_1R_2$ group can be combined with $R_1$ or $R_2$ of another $NR_1R_2$ group, or with $R_3$ or $R_4$ of a $NR_3R_4$ group, to form a substituted or unsubstituted, saturated or unsaturated cyclic group; $R_3$ and $R_4$ are the same or different and are a hydrocarbon group or a heteroatom-containing group; $R_3$ and $R_4$ can be combined to form a substituted or unsubstituted, saturated or unsaturated cyclic group; $R_3$ or $R_4$ of one $NR_3R_4$ group can be combined with $R_3$ or $R_4$ of another $NR_3R_4$ group, or with $R_1$ or $R_2$ of a $NR_1R_2$ group, to form a substituted or unsubstituted, saturated or unsaturated cyclic group; x is a value of at least 1; y is a value of at least 1; x+y is equal to the oxidation state of M; and wherein (i) $NR_3R_4$ has a steric bulk sufficiently large such that, due to steric hinderance, x cannot be a value equal to the oxidation state of M, (ii) $NR_1R_2$ has a steric bulk sufficiently small such that, due to lack of steric hinderance, y can be a value equal to the oxidation state of M only in the event that x is not a value of at least 1, and (iii) $NR_3R_4$ and $NR_1R_2$ have a steric bulk sufficient to maintain a heteroleptic structure in which x+y is equal to the oxidation state of M.

This invention further relates in part to organometallic precursors represented by the formulae above.

This invention yet further relates in part to a process for the production of a heteroleptic organometallic compound comprising reacting a homoleptic organometallic compound with a hydrocarbon compound or a heteroatom-containing compound in the presence of a solvent and under reaction conditions sufficient to produce said heteroleptic organometallic compound, wherein said heteroleptic organometallic compound is represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M. The organometallic compound yield resulting from the process of this invention can be 60% or greater, preferably 75% or greater, and more preferably 90% or greater.

This invention also relates in part to a method for producing a film, coating or powder by decomposing an organometallic precursor compound represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; thereby producing the film, coating or powder. Typically, the decomposing of said organometallic precursor compound is thermal, chemical, photochemical or plasma-activated.

This invention further relates in part to organometallic precursor compound mixtures comprising (a) an organometallic precursor compound represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; and (b) one or more different organometallic precursor compounds (e.g., a hafnium-containing, aluminum-containing, strontium-containing, barium-containing, or titanium-containing organometallic precursor compound).

This invention relates in particular to 'next generation' depositions involving heteroleptic-based metal precursors. These precursors can have advantages over the other known precursors. These heteroleptic materials can be used for a variety of purposes such as dielectrics, barriers, and electrodes, and in many cases show improved properties (thermal stability, desired morphology, less diffusion, lower leakage, less charge trapping, and the like) than other metal containing films.

The invention has several advantages. For example, the heteroleptic organometallic precursor compounds can provide a variety of desired properties, including access to single source precursors for multiple component films, improved affinity for substrates allowing for increased nucleation, decreased charge trapping, and/or increased conformality, and access to more viable liquid precursors (versus solids) with acceptable vapor pressures. The heteroleptic organometallic compounds of this invention can partially contain ligands with relatively sterically encumbering substituents, allowing for isolation of essentially pure heteroleptic organometallic compounds. The processes of the invention are useful in generating heteroleptic organometallic compounds that have varied chemical structures and physical properties. Films generated from the heteroleptic organometallic compound precursors can be deposited with a short incubation time, and the films deposited from the heteroleptic organometallic compound precursors exhibit good smoothness.

This invention relates in particular to chemical vapor deposition and atomic layer deposition precursors for next generation devices, specifically heteroleptic organometallic precursors are preferred that are liquid at room temperature, i.e., 20° C.

The heteroleptic organometallic precursor compounds of this invention can provide desired properties of an atomic layer deposition precursor for applications involving nanolaminate structures in tandem with other materials, for example, a material such as $Al_2O_3$.

DETAILED DESCRIPTION OF THE INVENTION

For heteroleptic systems described herein, certain advantages include one portion of the molecule being made more reactive/accessible to a substrate/co-reactant by having ligands of differing characteristics (sterically or electronically) on the central element, single-source precursor capability, (e.g., for hafnium silicates by utilizing a trimethylsilyl-containing amide bound to hafnium), and the precursors can be liquid compounds at room temperature, and thus easier to handle and utilize. As a result of this invention, more single-source precursors can be available for multiple component films allowing for simpler processing and less ampoules/lines on tools. Improved reactivity with substrates may allow for faster processing times and better film/device performance. The heteroleptic liquid precursors are easier to purify and transfer and provide simpler and more consistent process delivery.

A thermodynamic limit for ligand exchange is important for the heteroleptic organometallic compounds of this invention. By utilizing a bulky ligand, no additional ligand exchanges can take place. For example, if M* is a metal, S* is a small ligand, and L* is a large ligand, the starting hypothesis is that $M^*(S^*)_x$ exists and $M^*(L^*)_x$ does not (where x is equal to the oxidation state of the metal). Therefore, if excess L* (in whatever pre-coordination state is best appropriate) is combined with $M^*(S^*)_x$, ligand exchange will occur only to the point where no additional L* ligands will 'fit', yielding a discrete molecule of the formula $M^*(S^*)_{x-y}(L^*)_y$ (where y=1 to x−1) At that point, not only will the reaction stop, but no additional intermolecular net-ligand exchanges will be able to occur. Although S* and L* ligands may or may not exchange with other ligands of the same size, a S* ligand will be unable to exchange with a L* ligand because to do so would be to place one too many L* ligands around a metal based on thermodynamics. This synthetic process and the use of a bulky ligand is an important aspect of this invention.

As indicated above, this invention relates to heteroleptic organometallic compounds represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which $x+y$ is equal to the oxidation state of M.

More particularly, this invention relates to heteroleptic organometallic compounds represented by the formula $(R_4R_3N)_xM(NR_1R_2)_y$ wherein M is a metal or metalloid; $NR_1R_2$ and $NR_3R_4$ are different; $R_1$ and $R_2$ are the same or different and are a hydrocarbon group or a heteroatom-containing group; $R_1$ and $R_2$ can be combined to form a substituted or unsubstituted, saturated or unsaturated cyclic group; $R_1$ or $R_2$ of one $NR_1R_2$ group can be combined with $R_1$ or $R_2$ of another $NR_1R_2$ group, or with $R_3$ or $R_4$ of a $NR_3R_4$ group, to form a substituted or unsubstituted, saturated or unsaturated cyclic group; $R_3$ and $R_4$ are the same or different and are a hydrocarbon group or a heteroatom-containing group; $R_3$ and $R_4$ can be combined to form a substituted or unsubstituted, saturated or unsaturated cyclic group; $R_3$ or $R_4$ of one $NR_3R_4$ group can be combined with $R_3$ or $R_4$ of another $NR_3R_4$ group, or with $R_1$ or $R_2$ of a $NR_1R_2$ group, to form a substituted or unsubstituted, saturated or unsaturated cyclic group; x is a value of at least 1; y is a value of at least 1; x+y is equal to the oxidation state of M; and wherein (i) $NR_3R_4$ has a steric bulk sufficiently large such that, due to steric hinderance, x cannot be a value equal to the oxidation state of M, (ii) $NR_1R_2$ has a steric bulk sufficiently small such that, due to lack of steric hinderance, y can be a value equal to the oxidation state of M only in the event that x is not a value of at least 1, and (iii) $NR_3R_4$ and $NR_1R_2$ have a steric bulk sufficient to maintain a heteroleptic structure in which x+y is equal to the oxidation state of M. The heteroleptic organometallic compounds of this invention are preferably a liquid at 20° C.

For the heteroleptic organometallic compounds of this invention, $L_1$ preferably has a steric bulk equal to or greater than the steric bulk of diisopropylamide. $L_2$ preferably has a steric bulk equal to or less than the steric bulk of diisopropylamide. $NR_3R_4$ preferably has a steric bulk equal to or greater than the steric bulk of diisopropylamide. $NR_1R_2$ preferably has a steric bulk equal to or less than the steric bulk of diisopropylamide.

$L_1$ and $L_2$ are different and are independently hydrogen, a substituted or unsubstituted, saturated or unsaturated, aliphatic hydrocarbon, aromatic hydrocarbon, cycloaliphatic hydrocarbon, aliphatic heteroatom-containing group, aromatic heterocycle, cycloaliphatic heterocycle, or mixtures thereof. Illustrative $L_1$ and $L_2$ groups include, for example, hydrogen, alkyl, alkyl halide, silylated hydrocarbon, ether, polyether, thioether, ester, lactone, amide, amine, polyamine, nitrile, or mixtures thereof. $L_1$ and $L_2$ groups can also include substituted or unsubstituted, saturated or unsaturated, cyclic amido or amino groups, for example, aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl. For compounds in which x is a value greater than 1, the $L_1$ groups can be the same or different. For compounds in which y is a value greater than 1, the $L_2$ groups can be the same or different.

Typically, $R_1$, $R_2$, $R_3$ and $R_4$ are the same or different (as long as $NR_1R_2$ and $NR_3R_4$ are different) and are independently hydrogen, a substituted or unsubstituted, saturated or unsaturated, aliphatic hydrocarbon, aromatic hydrocarbon, or cycloaliphatic hydrocarbon. More particularly, $R_1$, $R_2$, $R_3$ and $R_4$ are the same or different (as long as $NR_1R_2$ and $NR_3R_4$ are different) and are independently hydrogen, methyl, ethyl, propyl, isopropyl, butyl, isobutyl, sec-butyl, tert-butyl, tert-amyl, cyclohexyl, adamantyl, phenyl, benzyl, silyl, dimethylsilyl, diethylsilyl, trimethylsilyl, triethylsilyl, dimethylethylsilyl, diethylmethylsilyl, and the like. Preferably, each of $R_1$, $R_2$, $R_3$ and $R_4$ is the same or different (as long as $NR_1R_2$ and $NR_3R_4$ are different) and is independently hydrogen, substituted or unsubstituted alkyl, or mixtures thereof. For compounds in which x is a value greater than 1, the $NR_3R_4$ groups can be the same or different. For compounds in which y is a value greater than 1, the $NR_1R_2$ groups can be the same or different.

Typically, M is a Group 2 (e.g., Sr, Ba) Group 3 (e.g., Sc, Y), Group 4 (Ti, Zr, Hf), Group 13 (Al, Ga) or a lanthanide series element (e.g., La, Ce, Pr, Nd, Dy, Er, and Yb). M can also be a Group 1, 5, 6, 7, 8, 9, 10, 11, 12, 14, 15, 16, 17, 18 or an actinide series element. M is preferably selected from a Group 2 element, a Group 13 element, a Group 14 element, a transition metal, or a lanthanide series element. More preferably, M is selected from Si, Ti, Zr, Hf, V, Nb, Ta, Cr, Mo, W, Sr, Ba, Sc, Y, Al, Ge, Ga, La, Ce, Pr, Nd, Sm, Eu, Gd, Tb, Dy, Ho, Er, Tm, Yb, and Lu.

Heteroleptic organometallic compounds of this invention include, for example, amides, cyclopentadienides, halides, beta-diketonates, alkyls, carbonyls, and the like. Illustrative heteroleptic organometallic compounds of this invention include, for example, bis(diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium, bis(ethylmethylamino)bis(diisopropylamino)titanium, bis(ethylmethylamino)bis(diisopropylamino)molybdenum, bis(ethylmethylamino)bis(diisopropylamino)tungsten, bis(diethylamino)bis(diisopropylamino)hafnium bis(diethylamino)bis(diisopropylamino)zirconium, bis(diethylamino)bis(diisopropylamino)titanium, bis(diethylamino)bis(diisopropylamino)molybdenum, bis(diethylamino)bis(diisopropylamino)tungsten, tris(diisopropylamino)(dimethylamino)hafnium tris(diisopropylamino)(dimethylamino)zirconium, tris(diisopropylamino)(dimethylamino)titanium, tris(diisopropylamino)(dimethylamino)molybdenum, tris(diisopropylamino)(dimethylamino)tungsten, tris(diethylamino)(diisopropylamino)hafnium, tris(diethylamino)(diisopropylamino)zirconium, tris(diethylamino)(diisopropylamino)titanium, tris(diethylamino)(diisopropylamino)molybdenum, tris(diethylamino)(diisopropylamino)tungsten, bis(dimethylamino)bis(bis(trimethylsilyl)amino)hafnium, bis(dimethylamino)bis(bis(trimethylsilyl)amino)zirconium, bis(dimethylamino)bis(bis(trimethylsilyl)amino)titanium, bis(dimethylamino)bis(bis(trimethylsilyl)amino)molybdenum, bis(dimethylamino)bis(bis(trimethylsilyl)amino)tungsten, tris(dimethylamino)(bis(trimethylsilyl)amino)hafnium, tris(dimethylamino)(bis(trimethylsilyl)amino)zirconium, tris(dimethylamino)(bis(trimethylsilyl)amino)titanium, tris(dimethylamino)(bis(trimethylsilyl)amino)molybdenum, tris(dimethylamino)

(bis(trimethylsilyl)amino)tungsten, tris(diethylamino)(dimethylamino)silane, bis(diisopropylamino)bis(dimethylamino)silane, (t-butylimino)diisopropylaminobis(dimethylamino)tantalum, bis(diisopropylamino)tris(dimethylamino)tantalum, bis(diisopropylamino)tris(dimethylamino)niobium, (di-t-butylamino)bis(bis(trimethylsilyl)amino)lanthanum, di-t-buylamino)bis(cyclopentadienyl)lanthanum, and the like. Preferred organometallic compounds include, for example, bis(diisopropylamino)bis(dimethylamino)hafnium, bis(diisopropylamino)bis(dimethylamino)zirconium, bis(dimethylamino)bis(bis(trimethylsilyl)amino)hafnium, (t-butylimino)diisopropylaminobis(dimethylamino)tantalum, and bis(diisopropylamino)tris(dimethylamino)tantalum.

It has been found that preparing more sterically congested compounds for a number of elements (depending on radius) can be difficult. For example, although hafnium forms 4-coordinate diethylamide compounds, a silicon (smaller atomic radius) analog has not been reported. However, a 4-coordinate dimethylamide complex is stable for silicon. Furthermore, cleanly isolating a 4-coordinate diisopropylamide hafnium complex from HfCl$_4$ is challenging. The unbranched dipropyl analog, however, has been isolated for hafnium. Since the electronics of these systems (i.e., the basicity of the parent amines) is similar, it is reasonable to conclude that steric congestion is the cause for these observations.

In accordance with an embodiment of this invention, the addition of an excess of a bulky amine (or other appropriate 'protonated' ligand) can be made to a homoleptic amide complex. For example, Hf(NMe$_2$)$_4$ can be added into a diisopropyl amine solution. The diisopropylamine can begin reacting with the homoleptic system, replacing randomly NMe$_2$ moieties. The resulting gaseous HNMe$_2$ can be kinetically scarce (compared to HN$^i$Pr$_2$), and can also be removed from the system via a nitrogen purge. The diisopropylamine has the kinetic opportunity to replace all the amides on hafnium. However, because the 4-coordinate diisopropylamide system is hypothesized to be difficult to access conventionally, the reaction should funnel to the most stable compound with the greatest number of diisopropylamide ligands, which should be greater than 0 but less than 4. By having the bulky amide in excess and allowing the volatile dimethylamine produced to leave the system, substituted dimethylamide ligands are not allowed to return to hafnium (thus kinetically driving the reaction). At the same time, because a bulky amide is being utilized, the dimethylamide ligands are not allowed to be fully replaced (thus thermodynamically limiting the reaction). The result is a heteroleptic system, namely Hf(NMe$_2$)$_x$(N$^i$Pr$_2$)$_{4-x}$ where in this case x=1, 2, or 3. Furthermore, the product should be predominantly one species as opposed to a statistical mixture of many compounds, thus facilitating purification.

By using this process, a number of heteroleptic systems may be accessible. For example, Si(NMe$_2$)$_x$(NEt$_2$)$_{4-x}$ (where x=1, 2, 3) may be possible. Also, bulkier amides can be used depending on the application. For example, reaction rate differences between the two amides present on the metal can be important. So an even bulkier ligand such as di-t-butylamide can be useful. Also, a single bulky bidentate diamide ligand can be useful. Although the 4-coordinate bis(trimethylsilyl) amide system may be too bulky to be stable around hafnium, generating a heteroleptic species by the methodology demonstrated herein can be useful for the development of a single source hafnium silicate precursor.

An illustrative synthetic scheme for production of heteroleptic amide compounds is given below.

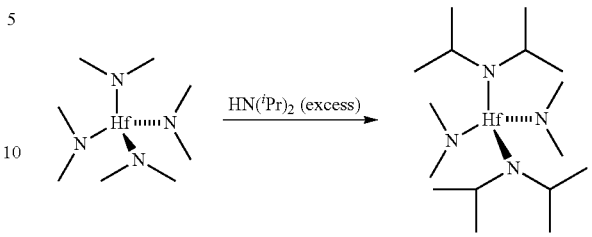

With respect to deposition, a major drawback of high k material integration, specifically in the gate stack, is increased charge trap density. These traps are associated with threshold voltage shifts and reliability problems. Although a large amount of electrical characterization data exists for these traps, there is little explanation regarding the cause (possible explanations for the charge traps are impurities, dangling bonds, as well as hydrogen and/or hydroxyl terminated metal atoms within the film, or at the interface). In addition, it appears that Al$_2$O$_3$ high k structures exhibit less electrical problems (implying less traps), compared to HfO$_2$. This may be attributed to differences in atomic structure, between films composed of Al$_2$O$_3$ and HfO$_2$, but there may also be some effect associated with the different number of ligands in the precursor molecules (aluminum compounds usually have 3 ligands and hafnium compounds have 4). The different number of ligands, and how they react, may affect the type and/or quantity of charge traps that are incorporated into the films.

Hafnium based materials deposited by atomic layer deposition require alternate pulses of a hafnium precursor and a coreactant (e.g., water), separated by a purge gas (e.g., nitrogen). Successive pulses of the hafnium precursor and the coreactant should result in half-reactions which are mutually dependent (i.e., they regenerate active sites for each other). One exemplary process for depositing HfO$_2$ by atomic layer deposition uses water and a hafnium amide (e.g., tetrakisdimethylamido hafnium). During each water pulse, the film surface is converted to hydroxyl groups. During each precursor pulse, the film surface is converted to amido ligands. In addition, prior to film growth, the surface termination of the substrate (e.g. silicon or silicon dioxide) must be converted to either hydroxyl or amido groups, in order to initiate the process. Ideally, the byproducts from this process are the corresponding amine (due to protonation of the amido ligands) and water (due to reaction of adjacent surface hydroxyl groups).

One proposed mechanism for this process is that, during the precursor pulse, as the precursor ligands react with a hydroxyl terminated surface, the lone pair electrons on the hydroxyl oxygen attack the hafnium metal center and the hydroxyl hydrogen then protonates the amido ligands. The resulting amine is volatile and desorbs from the surface. Due to steric effects, it is possible that 1, 2 or 3 out the 4 amido ligands can react with the hydroxyl groups on the surface during the precursor pulse. During the subsequent water pulse, the remaining amido ligands should be converted to amine, leaving hydroxyl groups on the surface.

The physical structure of hafnium oxide consists of hafnium atoms tetrahedrally bonded to oxygen atoms, in a crystalline (cubic) or amorphous solid. Ideally each oxygen atom bridges two hafnium atoms, although defects (e.g., impurity, dangling bond, hydroxyl termination) in the lattice are unavoidable. Reducing these defects, during the film deposition process, may result in better performance for high-k gate dielectric applications.

The majority of the hafnium precursors being investigated for atomic layer deposition of high k materials consist of 4 ligands, which are identical. There may be some effect on charge trap density due to the number of ligands that react during each half-reaction. In accordance with this invention, molecules may be tailored to incorporate mixed ligands, which have different reactivity towards surface hydroxyl groups and water vapor, and the number of ligands that react during each pulse can potentially be controlled. This can lead to films with decreased trap density. Assuming that ideally only two of the four ligands react during each pulse, it would be logical that the molecule has two ligands with the structure $R^1$, and two ligands with another structure $R^2$, for example $Hf(R^1)_2(R^2)_2$. $R^1$ and $R^2$ can be chosen from a wide variety of candidates, such as amido, alkoxide, halogen, and the like. If the number of ligands which react during the precursor pulse is different than 2, this changes (increases or decreases) the number of active sites available for reaction during growth of the next layer. The large number of charge traps that occur in hafnium based high k materials may be attributed to an uneven number of ligand removal, during each half-reaction.

While this invention has been described narrowly in some aspects for illustrative purposes, it is to be understood that modifications and variations can be included within the purview of this invention and the spirit and scope of the claims. For example, the atomic layer deposition techniques described herein may also provide better quality films which are deposited by chemical vapor deposition; the ligand family of $R^1$ and $R^2$ can be different or the same (e.g., both $R^1$ and $R^2$ are amido (but different amido), $R^1$ is a halogen and $R^2$ is an amido, or $R^1$ is an alkoxide and $R^2$ is a amido) such as $Hf(NEt_2)_2(NMe_2)_2$, $Hf(O^tBu)_2(NMe_2)_2$, and $Hf(pyrrolidinyl)_2(NMe_2)_2$; the precursors can have elements other than Hf (e.g., Zr); and the active sites mentioned hereinabove (e.g., hydroxyl and amido) can be different (e.g., halogen, alkoxide, hydrogen, dangling bond, etc.).

As indicated above, this invention also relates to a process for the production of a heteroleptic organometallic compound comprising reacting a homoleptic organometallic compound with a hydrocarbon compound or a heteroatom-containing compound in the presence of a solvent and under reaction conditions sufficient to produce said heteroleptic organometallic compound, wherein said heteroleptic organometallic compound is represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M. The heteroleptic organometallic compound yield resulting from the process of this invention can be 60% or greater, preferably 75% or greater, and more preferably 90% or greater.

In the processes described herein, the homoleptic organometallic compound starting material may be selected from a wide variety of compounds known in the art. The invention herein most prefers homoleptic organometallic compounds selected from amides, cyclopentadienides, halides, beta-diketonates, alkyls, carbonyls, and the like. Illustrative homoleptic organometallic compounds include, for example, tetrakis(dimethylamino)hafnium, tetrakis(dimethylamino)zirconium, tetrakis(dimethylamino)titanium, tetrakis(dimethylamino)molybdenum, tetrakis(dimethylamino)tungsten, tetrakis(diethylamino)hafnium, tetrakis(diethylamino)zirconium, tetrakis(diethylamino)titanium, tetrakis(diethylamino)molybdenum, tetrakis(diethylamino)tungsten, pentakis(dimethylamino)tantalum, pentakis(dimethylamino)niobium, tris(bis(trimethylsilyl)amino)lanthanum, and the like.

The concentration of the homoleptic organometallic compound starting material can vary over a wide range, and need only be that minimum amount necessary to react with the hydrocarbon compound or heteroatom-containing compound. In general, depending on the size of the reaction mixture, homoleptic organometallic compound starting material concentrations in the range of from about 1 millimole or less to about 10,000 millimoles or greater, should be sufficient for most processes.

In the processes described herein, the hydrocarbon compound or heteroatom-containing compound may be selected from a wide variety of compounds known in the art. Illustrative hydrocarbon compounds and heteroatom-containing compounds include, for example, dimethylamide, ethylmethylamide, diethylamide, isopropylmethylamide, diisopropylamide, di-tert-amylamide, tert-butylisopropylamide, di-tert-butylamide, dicyclohexylamide, tert-butyltrimethylsilylamide, diethyltetramethyldisilazane (amide), hexamethyldisilazane (amide), t-butoxide, cyclopentadienide, methylcyclopentadienide, tetramethylcyclopentadienide, pyrrolide, 2,5-dimethylpyrrolide, carbon monoxide, chloride, and the like. Preferred hydrocarbon compound or heteroatom-containing compound starting materials can be represented by the formula $NR_1R_2$ and $NR_3R_4$ wherein $NR_1R_2$ and $NR_3R_4$ are different; $R_1$ and $R_2$ are the same or different and are a hydrocarbon group or a heteroatom-containing group; $R_1$ and $R_2$ can be combined to form a substituted or unsubstituted, saturated or unsaturated cyclic group; $R_1$ or $R_2$ of one $NR_1R_2$ group can be combined with $R_1$ or $R_2$ of another $NR_1R_2$ group, or with $R_3$ or $R_4$ of a $NR_3R_4$ group, to form a substituted or unsubstituted, saturated or unsaturated cyclic group; $R_3$ and $R_4$ are the same or different and are a hydrocarbon group or a heteroatom-containing group; $R_3$ and $R_4$ can be combined to form a substituted or unsubstituted, saturated or unsaturated cyclic group; $R_3$ or $R_4$ of one $NR_3R_4$ group can be combined with $R_3$ or $R_4$ of another $NR_3R_4$ group, or with $R_1$ or $R_2$ of a $NR_1R_2$ group, to form a substituted or unsubstituted, saturated or unsaturated cyclic group.

In accordance with this invention, each of $R_1$, $R_2$, $R_3$ and $R_4$ can be hydrogen, a substituted or unsubstituted, saturated or unsaturated, hydrocarbon, aromatic hydrocarbon, cycloaliphatic hydrocarbon, aromatic heterocycle, alkyl halide, alkyl, silylated hydrocarbon, ether, polyether, thioether, ester, lactone, amide, amine, polyamine, nitrile; or mixtures thereof. The amine compounds can include cyclic and chelating systems. The amine compounds can also include the HCl salt of amines such as ammonium chloride, dimethylammonium chloride, and the like. Preferred amine compounds include, for example, dimethylamine, ethylmethylamine, isopropylmethylamine, diisopropylamine, hexamethyldisilazane, di-tert-amylamine, tert-butylisopropylamine, di-tert-butylamine, tert-butyltrimethylsilylamine, and diethyltetramethyldisilazane.

The concentration of the hydrocarbon compound or heteroatom-containing compound starting material can vary over a wide range, and need only be that minimum amount necessary to react with the homoleptic organometallic compound. In general, depending on the size of the reaction mixture, hydrocarbon compound or heteroatom-containing compound starting material concentrations in the range of from about 1 millimole or less to about 10,000 millimoles or greater, should be sufficient for most processes.

The solvent employed in the processes of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, nitriles, silicone oils, other aprotic solvents, or mixtures of one or more of the above; more preferably, pentanes, heptanes, octanes, nonanes, decanes, xylene, tetramethylbenzene, dimethoxyethanes, diglyme, fluorinated hydrocarbons, and mixtures of one or more of the above; and most preferably hexanes, ethers, THF, benzene, toluene, and mixtures of one of more of the above. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the processes for the reaction of the homoleptic organometallic compound and the hydrocarbon compound or heteroatom-containing compound, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 80° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

The heteroleptic organometallic compounds prepared from the reaction of the homoleptic organometallic compound starting material and the hydrocarbon compound or heteroatom-containing compound starting material may be selected from a wide variety of compounds. Heteroleptic organometallic compounds prepared by the process of this invention include, for example, amides, cyclopentadienides, halides, beta-diketonates, alkyls, carbonyls, and the like. Illustrative heteroleptic organometallic compounds prepared by the process of this invention include, for example, bis (diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium, bis(ethylmethylamino)bis(diisopropylamino)titanium, bis(ethylmethylamino)bis(diisopropylamino)molybdenum, bis(ethylmethylamino)bis(diisopropylamino)tungsten, bis(diethylamino)bis(diisopropylamino)hafnium bis(diethylamino)bis(diisopropylamino)zirconium, bis(diethylamino)bis(diisopropylamino)titanium, bis(diethylamino)bis(diisopropylamino)molybdenum, bis(diethylamino)bis(diisopropylamino)tungsten, tris(diisopropylamino)(dimethylamino)hafnium tris(diisopropylamino)(dimethylamino)zirconium, tris(diisopropylamino)(dimethylamino)titanium, tris(diisopropylamino)(dimethylamino)molybdenum, tris(diisopropylamino)(dimethylamino)tungsten, tris(diethyl amino)(diisopropylamino)hafnium, tris(diethylamino)(diisopropylamino)zirconium, tris(diethylamino)(diisopropylamino)titanium, tris(diethylamino)(diisopropylamino)molybdenum, tris(diethylamino)(diisopropylamino)tungsten, bis(dimethylamino)bis(bis(trimethylsilyl)amino)hafnium, bis(dimethylamino)bis(bis(trimethylsilyl)amino)zirconium, bis(dimethylamino)bis(bis(trimethylsilyl)amino)titanium, bis(dimethylamino)bis(bis(trimethylsilyl)amino)molybdenum, bis(dimethylamino)bis(bis(trimethylsilyl)amino)tungsten, tris(dimethylamino)(bis(trimethylsilyl)amino)hafnium, tris(dimethylamino)(bis(trimethylsilyl)amino)zirconium, tris(dimethylamino)(bis(trimethylsilyl)amino)titanium, tris(dimethylamino)(bis(trimethylsilyl)amino)molybdenum, tris(dimethylamino)(bis(trimethylsilyl)amino)tungsten, tris(diethylamino)(dimethylamino)silane, bis(diisopropylamino)bis(dimethylamino)silane, (t-butylimino)diisopropylaminobis(dimethylamino)tantalum, bis(diisopropylamino)tris(dimethylamino)tantalum, bis(diisopropylamino)tris(dimethylamino)niobium, (di-t-butylamino)bis(bis(trimethylsilyl)amino)lanthanum, di-t-buylamino)bis(cyclopentadienyl)lanthanum, and the like.

For organometallic compounds prepared by the processes of this invention, purification can occur through recrystallization, more preferably through extraction of reaction residue (e.g., hexane) and chromatography, and most preferably through sublimation and distillation.

Those skilled in the art will recognize that numerous changes may be made to the processes described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are preferably liquid at room temperature, i.e., 20° C., and are well suited for preparing in-situ powders and coatings. For instance, a liquid organometallic compound precursor can be applied to a substrate and then heated to a temperature sufficient to decompose the precursor, thereby forming a metal or metal oxide coating on the substrate. Applying a liquid precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Liquid organometallic compound precursors such as described above also can be atomized and sprayed onto a substrate. Atomization and spraying means, such as nozzles, nebulizers and others, that can be employed are known in the art.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention relates to organometallic precursor compound mixtures comprising (a) an organometallic precursor compound represented by the formula $(L_1)_xM(L_2)_y$, wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; and (b) one or more different organometallic precursor compounds (e.g., a hafnium-containing, aluminum-containing, strontium-containing, barium-containing, titanium-containing organometallic precursor compound).

Deposition can be conducted in the presence of other gas phase components. In an embodiment of the invention, film deposition is conducted in the presence of at least one non-reactive carrier gas. Examples of non-reactive gases include inert gases, e.g., nitrogen, argon, helium, as well as other gases that do not react with the organometallic compound precursor under process conditions. In other embodiments, film deposition is conducted in the presence of at least one reactive gas. Some of the reactive gases that can be employed include but are not limited to hydrazine, oxygen, hydrogen, air, oxygen-enriched air, ozone ($O_3$), nitrous oxide ($N_2O$), water vapor, organic vapors, ammonia and others. As known in the art, the presence of an oxidizing gas, such as, for example, air, oxygen, oxygen-enriched air, $O_3$, $N_2O$ or a vapor of an oxidizing organic compound, favors the formation of a metal oxide film.

As indicated above, this invention also relates in part to a method for producing a film, coating or powder. The method includes the step of decomposing at least one organometallic compound precursor, thereby producing the film, coating or powder, as further described below. More particularly, this invention relates in part to a method for producing a film, coating or powder by decomposing an organometallic precursor compound represented by the formula $(L_1)_xM(L_2)_y$, wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; thereby producing the film, coating or powder. Typically, the decomposing of said organometallic precursor compound is thermal, chemical, photochemical or plasma-activated.

Deposition methods described herein can be conducted to form a film, powder or coating that includes a single metal or a film, powder or coating that includes a single metal oxide. Mixed films, powders or coatings also can be deposited, for instance mixed metal oxide films. A mixed metal oxide film can be formed, for example, by employing several organometallic precursors, at least one of which being selected from the organometallic compounds described above.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metalorganic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, Ta; metal aluminates; metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); barrier materials, e.g., TiN, TaN; or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

Chemical vapor deposition films can be deposited to a desired thickness. For example, films formed can be less than 1 micron thick, preferably less than 500 nanometer and more preferably less than 200 nanometers thick. Films that are less than 50 nanometer thick, for instance, films that have a thickness between about 1 and about 20 nanometers, also can be produced.

Organometallic compound precursors described above also can be employed in the method of the invention to form films by atomic layer deposition (ALD) or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$.

In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate. Metal oxide films also can be formed, for example by using an oxidizing gas.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal oxide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal oxide. Mixed films also can be deposited, for instance mixed metal oxide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

Atomic layer deposition and chemical vapor deposition of silicates and aluminates can be useful for many next generation materials (e.g., lanthanum aluminates for dielectrics).

Various modifications and variations of this invention will be obvious to a worker skilled in the art and it is to be understood that such modifications and variations are to be included within the purview of this application and the spirit and scope of the claims.

Example 1

Synthesis of bis(dimethylamino)bis(bis(trimethylsilyl)amino)hafnium

To a dry, nitrogen purged, 100 milliliter round-bottom flask charged with a magnetic stir bar was added anhydrous hexanes (25 milliliters). Hf(NMe$_2$)$_4$ (5.00 grams, 0.014 mol) was added via syringe, followed by HN(SiMe$_3$)$_2$ (13.65 grams, 0.085 mol). The flask was fitted with a condenser, and the contents refluxed for about 1 hour. After cooling to room temperature, the hexanes and excess amine were removed under reduced pressure to yield the crude product, which can be further purified by sublimation/distillation. $^1$H NMR indicated Hf-bound —NMe$_2$ and —N(SiMe$_3$)$_2$ resonances.

The invention claimed is:

1. A heteroleptic organometallic compound represented by the formula (L$_1$)$_x$M(L$_2$)$_y$ wherein M is a metal or metalloid, L$_1$ and L$_2$ are different and are selected from hydrogen, a substituted or unsubstituted, saturated or unsaturated, aliphatic hydrocarbon, aromatic hydrocarbon, cycloaliphatic hydrocarbon, aliphatic heteroatom-containing group, aromatic heterocycle, cycloaliphatic heterocycle, or mixtures thereof; x is a value of at least 1; y is a value of at least 1; x+y is equal to the oxidation state of M; and wherein (i) L$_1$ has a steric bulk sufficiently large such that, due to steric hinderance, x cannot be a value equal to the oxidation state of M, (ii) L$_2$ has a steric bulk sufficiently small such that, due to lack of steric hinderance, y can be a value equal to the oxidation state of M only in the event that x is not a value of at least 1, and (iii) L$_1$ and L$_2$ have a steric bulk sufficient to maintain a heteroleptic structure in which x+y is equal to the oxidation state of M; wherein said heteroleptic organometallic compound is a liquid at 20° C.

2. The heteroleptic organometallic compound of claim 1 represented by the formula (R$_4$R$_3$N)$_x$M(NR$_1$R$_2$)$_y$ wherein M is a metal or metalloid; NR$_1$R$_2$ and NR$_3$R$_4$ are different; R$_1$ and R$_2$ are the same or different and are a hydrocarbon group or a heteroatom-containing group; R$_1$ and R$_2$ can be combined to form a substituted or unsubstituted, saturated or unsaturated cyclic group; R$_1$ or R$_2$ of one NR$_1$R$_2$ group can be combined with R$_1$ or R$_2$ of another NR$_1$R$_2$ group, or with R$_3$ or R$_4$ of a NR$_3$R$_4$ group, to form a substituted or unsubstituted, saturated or unsaturated cyclic group; R$_3$ and R$_4$ are the same or different and are a hydrocarbon group or a heteroatom-containing group; R$_3$ and R$_4$ can be combined to form a substituted or unsubstituted, saturated or unsaturated cyclic group; R$_3$ or R$_4$ of one NR$_3$R$_4$ group can be combined with R$_3$ or R$_4$ of another NR$_3$R$_4$ group, or with R$_1$ or R$_2$ of a NR$_1$R$_2$ group, to form a substituted or unsubstituted, saturated or unsaturated cyclic group; x is a value of at least 1; y is a value of at least 1; x+y is equal to the oxidation state of M; and wherein (i) NR$_3$R$_4$ has a steric bulk sufficiently large such that, due to steric hinderance, x cannot be a value equal to the oxidation state of M, (ii) NR$_1$R$_2$ has a steric bulk sufficiently small such that, due to lack of steric hinderance, y can be a value equal to the oxidation state of M only in the event that x is not a value of at least 1, and (iii) NR$_3$R$_4$ and NR$_1$R$_2$ have a steric bulk sufficient to maintain a heteroleptic structure in which x+y is equal to the oxidation state of M.

3. The heteroleptic organometallic compound of claim 1 wherein M is selected from a Group 2 element, a Group 4 element, a Group 13 element, a Group 14 element, a transition metal, a lanthanide series element or an actinide series element.

4. The heteroleptic organometallic compound of claim 1 wherein M is selected from Si, Ti, Zr, Hf, V, Nb, Ta, Cr, Mo, W, Sr, Ba, Sc, Y, Al, Ge, Ga, La, Ce, Pr, Nd, Sm, Eu, Gd, Tb, Dy, Ho, Er, Tm, Yb, and Lu.

5. The heteroleptic organometallic compound of claim 1 wherein L$_1$ and L$_2$ are different and are independently selected from hydrogen, alkyl, alkyl halide, silylated hydrocarbon, ether, polyether, thioether, ester, lactone, amide, amine, polyamine, nitrile, or mixtures thereof.

6. The heteroleptic organometallic compound of claim 1 wherein L$_1$ and L$_2$ are different and are independently selected from a substituted or unsubstituted, saturated or unsaturated, cyclic amido or amino group comprising aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl; or wherein L$_1$ and L$_2$ are different and are independently selected from dimethylamide, ethylmethylamide, diethylamide, isopropylmethylamide, diisopropylamide, di-tert-amylamide, tert-butylisopropylamide, di-tert-butylamide, dicyclohexylamide, tert-butyltrimethylsilylamide, diethyltetramethyldisilazane (amide), hexamethyldisilazane (amide), and t-butoxide.

7. The heteroleptic organometallic compound of claim 1 wherein, when x is a value greater than 1, each L$_1$ group is the same or different; or wherein, when y is a value greater than 1, each L$_2$ group is the same or different.

8. The heteroleptic organometallic compound of claim 2 wherein R$_1$, R$_2$, R$_3$ and R$_4$ are the same or different and are independently selected from hydrogen, a substituted or unsubstituted, saturated or unsaturated, aliphatic hydrocarbon, aromatic hydrocarbon, or cycloaliphatic hydrocarbon, provided NR$_1$R$_2$ and NR$_3$R$_4$ are different.

9. The heteroleptic organometallic compound of claim 2 wherein R$_1$, R$_2$, R$_3$ and R$_4$ are the same or different and are independently selected from hydrogen, methyl, ethyl, propyl, isopropyl, butyl, isobutyl, sec-butyl, tert-butyl, tert-amyl, cyclohexyl, adamantyl, phenyl, benzyl, silyl, dimethylsilyl, diethylsilyl, trimethylsilyl, triethylsilyl, dimethylethylsilyl, or diethylmethylsilyl, provided NR$_1$R$_2$ and NR$_3$R$_4$ are different; or wherein R$_1$, R$_2$, R$_3$ and R$_4$ are the same or different and are independently selected from hydrogen or substituted or unsubstituted alkyl, provided NR$_1$R$_2$ and NR$_3$R$_4$ are different.

10. The heteroleptic organometallic compound of claim 1 in which L$_1$ has a steric bulk equal to or greater than the steric bulk of diisopropylamide, or in which L$_2$ has a steric bulk equal to or less than the steric bulk of diisopropylamide.

11. The heteroleptic organometallic compound of claim 2 in which NR$_3$R$_4$ has a steric bulk equal to or greater than the steric bulk of diisopropylamide, or in which NR$_1$R$_2$ has a steric bulk equal to or less than the steric bulk of diisopropylamide.

12. The heteroleptic organometallic compound of claim 1 selected from amides, cyclopentadienides, halides, beta-diketonates, alkyls, and carbonyls.

13. The heteroleptic organometallic compound of claim 1 selected from bis(diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium bis(ethylmethylamino)bis(diisopropylamino)titanium bis(ethylmethylamino)bis(diisopropylamino)molybdenum, bis(ethylmethylamino)bis(diisopropylamino)tungsten bis(diethylamino)bis(diisopropylamino)hafnium bis(diethylamino)bis(diisopropylamino)zirconium bis(diethylamino)bis(diisopropylamino)titanium bis(diethylamino)bis (diisopropylamino)molybdenum, (diisopropylamino)tungsten, (dimethylamino)hafnium (dimethylamino)zirconium, (dimethylamino)titanium, (dimethylamino)molybdenum, (dimethylamino)tungsten, (diisopropylamino)hafnium, (diisopropylamino)zirconium, (diisopropylamino)titanium, (diisopropylamino)molybdenum, (diisopropylamino)tungsten, bis(dimethylamino)bis(bis (trimethylsilyl)amino)hafnium, bis(dimethylamino)bis(bis (trimethylsilyl)amino)zirconium, bis(dimethylamino)bis(bis (trimethylsilyl)amino)titanium, bis(dimethylamino)bis(bis (trimethylsilyl)amino)molybdenum, bis(dimethylamino)bis (bis(trimethylsilyl)amino)tungsten, tris(dimethylamino)(bis (trimethylsilyl)amino)hafnium, tris(dimethylamino)(bis (trimethylsilyl)amino)zirconium, tris(dimethylamino)(bis (trimethylsilyl)amino)titanium, tris(dimethylamino)(bis (trimethylsilyl)amino)molybdenum, tris(dimethylamino) (bis(trimethylsilyl)amino)tungsten, tris(diethylamino) (dimethylamino)silane, bis(diisopropylamino)bis (dimethylamino)silane, (t-butylimino)diisopropylaminobis (dimethylamino)tantalum, bis(diisopropylamino)tris (dimethylamino)tantalum, bis(diisopropylamino)tris (dimethylamino)niobium, (di-t-butylamino)bis(bis (trimethylsilyl)amino)lanthanum, and di-t-buylamino)bis (cyclopentadienyl)lanthanum.

14. A process for the production of a heteroleptic organometallic compound comprising reacting a homoleptic organometallic compound with a hydrocarbon compound or a heteroatom-containing compound in the presence of a solvent and under reaction conditions sufficient to produce said heteroleptic organometallic compound, wherein said heteroleptic organometallic compound is represented by the formula $(L_1)_xM(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hindrance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M.

15. The process of claim 14 wherein the homoleptic organometallic compound is selected from amides, cyclopentadienides, halides, beta-diketonates, alkyls, and carbonyls.

16. The process of claim 14 wherein the homoleptic organometallic compound is selected from tetrakis(dimethylamino)hafnium, tetrakis(dimethylamino)zirconium, tetrakis(dimethylamino)titanium, tetrakis(dimethylamino)molybdenum, tetrakis(dimethylamino)tungsten, tetrakis(diethylamino)hafnium, tetrakis(diethylamino)zirconium, tetrakis(diethylamino)titanium, tetrakis(diethylamino)molybdenum, tetrakis(diethylamino)tungsten, pentakis(dimethylamino)tantalum, pentakis(dimethylamino)niobium, and tris(bis(trimethylsilyl)amino)lanthanum; and the hydrocarbon compound or heteroatom-containing compound is selected from dimethylamide, ethylmethylamide, diethylamide, isopropylmethylamide, diisopropylamide, di-tert-amylamide, tert-butylisopropylamide, di-tert-butylamide, dicyclohexylamide, tert-butyltrimethylsilylamide, diethyltetramethyldisilazane (amide), hexamethyldisilazane (amide), t-butoxide, cyclopentadienide, methylcyclopentadienide, tetramethylcyclopentadienide, pyrrolides, 2,5-dimethylpyrrolide, carbon monoxide, and chlorides.

17. The process of claim 14 in which the heteroleptic organometallic compound is selected from bis(diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium, bis(ethylmethylamino)bis(diisopropylamino)titanium, bis(ethylmethylamino)bis(diisopropylamino)molybdenum, bis(ethylmethylamino)bis(diisopropylamino)tungsten, bis(diethylamino)bis(diisopropylamino)hafnium bis(diethylamino)bis(diisopropylamino)zirconium, bis(diethylamino)bis(diisopropylamino)titanium, bis(diethylamino)bis(diisopropylamino)molybdenum, bis(diethylamino)bis(diisopropylamino)tungsten, tris(diisopropylamino)(dimethylamino)hafnium tris(diisopropylamino)(dimethylamino)zirconium, tris(diisopropylamino)(dimethylamino)titanium, tris(diisopropylamino)(dimethylamino)molybdenum, tris(diisopropylamino)(dimethylamino)tungsten, tris(diethylamino)(diisopropylamino)hafnium, tris(diethylamino)(diisopropylamino)zirconium, tris(diethylamino)(diisopropylamino)titanium, tris(diethylamino)(diisopropylamino)molybdenum, tris(diethylamino)(diisopropylamino)tungsten, bis(dimethylamino)bis(bis(trimethylsilyl)amino)hafnium, bis(dimethylamino)bis(bis(trimethylsilyl)amino)zirconium, bis(dimethylamino)bis(bis(trimethylsilyl)amino)titanium, bis(dimethylamino)bis(bis(trimethylsilyl)amino)molybdenum, bis(dimethylamino)bis(bis(trimethylsilyl)amino)tungsten, tris(dimethylamino)(bis(trimethylsilyl)amino)hafnium, tris(dimethylamino)(bis(trimethylsilyl)amino)zirconium, tris(dimethylamino)(bis(trimethylsilyl)amino)titanium, tris(dimethylamino)(bis(trimethylsilyl)amino)molybdenum, tris(dimethylamino)(bis(trimethylsilyl)amino)tungsten, tris(diethylamino)(dimethylamino)silane, bis(diisopropylamino)bis(dimethylamino)silane, (t-butylimino)diisopropylaminobis(dimethylamino)tantalum, bis(diisopropylamino)tris(dimethylamino)tantalum, bis(diisopropylamino)tris(dimethylamino)niobium, (di-t-butylamino)bis(bis(trimethylsilyl)amino)lanthanum, and di-t-buylamino)bis(cyclopentadienyl)lanthanum.

18. The process of claim 14 wherein the heteroleptic organometallic compound yield is 60% or greater.

19. A method for producing a film, coating or powder by decomposing a heteroleptic organometallic precursor compound represented by the formula $(L_1)_xM(L_2)_y$ wherein M is a metal or metalloid, $L_1$ and $L_2$ are different and are selected from hydrogen, a substituted or unsubstituted, saturated or unsaturated, aliphatic hydrocarbon, aromatic hydrocarbon, cycloaliphatic hydrocarbon, aliphatic heteroatom-containing group, aromatic heterocycle, cycloaliphatic heterocycle, or mixtures thereof; x is a value of at least 1; y is a value of at least 1; x+y is equal to the oxidation state of M; and wherein (i) $L_1$ has a steric bulk sufficiently large such that, due to steric hindrance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; wherein said heteroleptic organometallic precursor compound is a liquid at 20° C.; thereby producing the film, coating or powder.

20. The method of claim 19 wherein the decomposing of said heteroleptic organometallic precursor compound is thermal, chemical, photochemical or plasma-activated.

21. The method of claim 19 wherein said heteroleptic organometallic precursor compound is vaporized and the vapor is directed into a deposition reactor housing a substrate.

22. The method of claim 21 wherein said substrate is comprised of a material selected from the group consisting of a metal, a metal silicide, a metal aluminate, a semiconductor, an insulator and a barrier material.

23. The method of claim 21 wherein said substrate is a patterned wafer.

24. The method of claim 19 wherein said film, coating or powder is produced by a gas phase deposition.

25. The method of claim 19 wherein said film, coating or powder is produced by a chemical vapor deposition or atomic layer deposition.

26. A mixture comprising (a) a heteroleptic organometallic precursor compound represented by the formula $(L_1)_xM(L_2)_y$, wherein M is a metal or metalloid, $L_1$ and $L_2$ are different and are selected from hydrogen, a substituted or unsubstituted, saturated or unsaturated, aliphatic hydrocarbon, aromatic hydrocarbon, cycloaliphatic hydrocarbon, aliphatic heteroatom-containing group, aromatic heterocycle, cycloaliphatic heterocycle, or mixtures thereof; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; wherein said heteroleptic organometallic precursor compound is a liquid at 20° C., and (b) one or more different organometallic precursor compounds.

27. The mixture of claim 26 wherein said one or more other organometallic precursor compounds are selected from a homoleptic organometallic precursor compound or a heteroleptic organometallic precursor compound.

28. The mixture of claim 26 wherein said one or more other organometallic precursor compounds are selected from a hafnium-containing, aluminum-containing, strontium-containing, barium-containing, or titanium-containing organometallic precursor compound.

29. A heteroleptic organometallic compound represented by the formula $(L_1)_xM(L_2)_y$, wherein M is a metal or metalloid, $L_1$ and $L_2$ are different and are independently selected from a substituted or unsubstituted, saturated or unsaturated, cyclic amido or amino group comprising aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl; or wherein $L_1$ and $L_2$ are different and are independently selected from dimethylamide, ethylmethylamide, diethylamide, isopropylmethylamide, diisopropylamide, di-tert-amylamide, tert-butylisopropylamide, di-tert-butylamide, dicyclohexylamide, tert-butyltrimethylsilylamide, diethyltetramethyldisilazane (amide), hexamethyldisilazane (amide), and t-butoxide; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M.

30. A heteroleptic organometallic compound represented by the formula $(L_1)_xM(L_2)_y$, wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; wherein said heteroleptic organometallic compound is selected from bis(diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium, bis(ethylmethylamino)bis(diisopropylamino)titanium, bis(ethylmethylamino)bis(diisopropylamino)molybdenum, bis(ethylmethylamino)bis(diisopropylamino)tungsten, bis(diethylamino)bis(diisopropylamino)hafnium bis(diethylamino)bis(diisopropylamino)zirconium, bis(diethylamino)bis(diisopropylamino)titanium, bis(diethylamino)bis(diisopropylamino)molybdenum, bis(diethylamino)bis(diisopropylamino)tungsten, tris(diisopropylamino)(dimethylamino)hafnium tris(diisopropylamino)(dimethylamino)zirconium, tris(diisopropylamino)(dimethylamino)titanium, tris(diisopropylamino)(dimethylamino)molybdenum, tris(diisopropylamino)(dimethylamino)tungsten, tris(diethylamino)(diisopropylamino)hafnium, tris(diethylamino)(diisopropylamino)zirconium, tris(diethylamino)(diisopropylamino)titanium, tris(diethylamino)(diisopropylamino)molybdenum, tris(diethylamino)(diisopropylamino)tungsten, bis(dimethylamino)bis(bis(trimethylsilyl)amino)hafnium, bis(dimethylamino)bis(bis(trimethylsilyl)amino)zirconium, bis(dimethylamino)bis(bis(trimethylsilyl)amino)titanium, bis(dimethylamino)bis(bis(trimethylsilyl)amino)molybdenum, bis(dimethylamino)bis(bis(trimethylsilyl)amino)tungsten, tris(dimethylamino)(bis(trimethylsilyl)amino)hafnium, tris(dimethylamino)(bis(trimethylsilyl)amino)zirconium, tris(dimethylamino)(bis(trimethylsilyl)amino)titanium, tris(dimethylamino)(bis(trimethylsilyl)amino)molybdenum, tris(dimethylamino)(bis(trimethylsilyl)amino)tungsten, tris(diethylamino)(dimethylamino)silane, bis(diisopropylamino)bis(dimethylamino)silane, (t-butylimino)diisopropylaminobis (dimethylamino)tantalum, bis(diisopropylamino)tris(dimethylamino)tantalum, bis(diisopropylamino)tris(dimethylamino)niobium, (di-t-butylamino)bis(bis(trimethylsilyl)amino)lanthanum, and di-t-buylamino)bis(cyclopentadienyl)lanthanum.

31. A method for producing a film, coating or powder by decomposing a heteroleptic organometallic precursor compound represented by the formula $(L_1)_x M(L_2)_y$ wherein M is a metal or metalloid, $L_1$ and $L_2$ are different and are independently selected from a substituted or unsubstituted, saturated or unsaturated, cyclic amido or amino group comprising aziridinyl, azetidinyl, pyrrolidinyl, thiazolidinyl, piperidinyl, pyrrolyl, pyridinyl, pyrimidinyl, pyrrolinyl, pyrazolyl, thiazolyl, oxazolyl, imidazolyl, imidazolidinonyl, imidazolidinethionyl, quinolinyl, isoquinolinyl, carbazolyl, triazolyl, indolyl and purinyl; or wherein $L_1$ and $L_2$ are different and are independently selected from dimethylamide, ethylmethylamide, diethylamide, isopropylmethylamide, diisopropylamide, di-tert-amylamide, tert-butylisopropylamide, di-tert-butylamide, dicyclohexylamide, tert-butyltrimethylsilylamide, diethyltetramethyldisilazane (amide), hexamethyldisilazane (amide), and t-butoxide; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; thereby producing the film, coating or powder.

32. A method for producing a film, coating or powder by decomposing a heteroleptic organometallic precursor compound represented by the formula $(L_1)_x M(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M; thereby producing the film, coating or powder; wherein said heteroleptic organometallic precursor compound is selected from bis(diisopropylamino)bis(dimethylamino)hafnium, bis(diisopropylamino)bis(dimethylamino)zirconium, bis(diisopropylamino)bis(dimethylamino)titanium, bis(diisopropylamino)bis(dimethylamino)molybdenum, bis(diisopropylamino)bis(dimethylamino)tungsten, bis(di-t-butylamino)bis(dimethylamino)hafnium, bis(di-t-butylamino)bis(dimethylamino)zirconium, bis(di-t-butylamino)bis(dimethylamino)titanium, bis(di-t-butylamino)bis(dimethylamino)molybdenum, bis(di-t-butylamino)bis(dimethylamino)tungsten, bis(ethylmethylamino)bis(diisopropylamino)hafnium bis(ethylmethylamino)bis(diisopropylamino)zirconium, bis(ethylmethylamino)bis(diisopropylamino)titanium, bis(ethylmethylamino)bis(diisopropylamino)molybdenum, bis(ethylmethylamino)bis(diisopropylamino)tungsten, bis(diethylamino)bis(diisopropylamino)hafnium bis(diethylamino)bis(diisopropylamino)zirconium, bis(diethylamino)bis(diisopropylamino)titanium, bis(diethylamino)bis(diisopropylamino)molybdenum, bis(diethylamino)bis(diisopropylamino)tungsten, tris(diisopropylamino)(dimethylamino)hafnium tris(diisopropylamino)(dimethylamino)zirconium, tris(diisopropylamino)(dimethylamino)titanium, tris(diisopropylamino)(dimethylamino)molybdenum, tris(diisopropylamino)(dimethylamino)tungsten, tris(diethylamino)(diisopropylamino)hafnium, tris(diethylamino)(diisopropylamino)zirconium, tris(diethylamino)(diisopropylamino)titanium, tris(diethylamino)(diisopropylamino)molybdenum, tris(diethylamino)(diisopropylamino)tungsten, bis(dimethylamino)bis(bis(trimethylsilyl)amino)hafnium, bis(dimethylamino)bis(bis(trimethylsilyl)amino)zirconium, bis(dimethylamino)bis(bis(trimethylsilyl)amino)titanium, bis(dimethylamino)bis(bis(trimethylsilyl)amino)molybdenum, bis(dimethylamino)bis(bis(trimethylsilyl)amino)tungsten, tris(dimethylamino)(bis(trimethylsilyl)amino)hafnium, tris(dimethylamino)(bis(trimethylsilyl)amino)zirconium, tris(dimethylamino)(bis(trimethylsilyl)amino)titanium, tris(dimethylamino)(bis(trimethylsilyl)amino)molybdenum, tris(dimethylamino)(bis(trimethylsilyl)amino)tungsten, tris(diethylamino)(dimethylamino)silane, bis(diisopropylamino)bis(dimethylamino)silane, (t-butylimino)diisopropylaminobis(dimethylamino)tantalum, bis(diisopropylamino)tris(dimethylamino)tantalum, bis(diisopropylamino)tris(dimethylamino)niobium, (di-t-butylamino)bis(bis(trimethylsilyl)amino)lanthanum, and di-t-buylamino)bis(cyclopentadienyl)lanthanum.

33. A mixture comprising (a) a heteroleptic organometallic precursor compound represented by the formula $(L_1)_x M(L_2)_y$ wherein M is a metal or metalloid, $L_1$ and $L_2$ are different and are each a hydrocarbon group or a heteroatom-containing group; x is a value of at least 1; y is a value of at least 1; x+y is equal to the oxidation state of M; and wherein (i) $L_1$ has a steric bulk sufficiently large such that, due to steric hinderance, x cannot be a value equal to the oxidation state of M, (ii) $L_2$ has a steric bulk sufficiently small such that, due to lack of steric hinderance, y can be a value equal to the oxidation state of M only in the event that x is not a value of at least 1, and (iii) $L_1$ and $L_2$ have a steric bulk sufficient to maintain a heteroleptic structure in which x+y is equal to the oxidation state of M, and (b) one or more different organometallic precursor compounds selected from a homoleptic organometallic precursor compound or a heteroleptic organometallic precursor compound.

* * * * *